United States Patent
Iimura (10) Patent No.: US 8,968,200 B2
(45) Date of Patent: Mar. 3, 2015

(54) ULTRASONIC ELASTOGRAPHY FOR CROSS SECTIONAL TISSUE MEASUREMENT METHOD AND APPARATUS

(75) Inventor: Takashi Iimura, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 377 days.

(21) Appl. No.: 12/735,857

(22) PCT Filed: Feb. 19, 2009

(86) PCT No.: PCT/JP2009/052829
§ 371 (c)(1),
(2), (4) Date: Aug. 20, 2010

(87) PCT Pub. No.: WO2009/104657
PCT Pub. Date: Aug. 27, 2009

(65) Prior Publication Data
US 2011/0004100 A1    Jan. 6, 2011

(30) Foreign Application Priority Data

Feb. 21, 2008  (JP) .................................. 2008-040688

(51) Int. Cl.
*A61B 8/14*     (2006.01)
*A61B 8/08*     (2006.01)
*G01S 7/52*     (2006.01)

(52) U.S. Cl.
CPC ............... *A61B 8/0833* (2013.01); *A61B 8/485* (2013.01); *G01S 7/52023* (2013.01); *G01S 7/52036* (2013.01); *G01S 7/52042* (2013.01); *G01S 7/52071* (2013.01); *G01S 7/52074* (2013.01)
USPC ............................ 600/438; 600/443; 382/128

(58) Field of Classification Search
CPC . G01S 7/52073; G01S 7/52042; A61B 8/485; A61B 8/0833
USPC .......................... 382/128, 131; 600/437, 443
See application file for complete search history.

(56) References Cited

U.S. PATENT DOCUMENTS

| | | | |
|---|---|---|---|
| 2007/0036411 A1* | 2/2007 | Guetat et al. | 382/128 |
| 2007/0123778 A1* | 5/2007 | Kantorovich | 600/437 |
| 2007/0167784 A1* | 7/2007 | Shekhar et al. | 600/443 |
| 2008/0021318 A1* | 1/2008 | Kato et al. | 600/437 |
| 2008/0123927 A1* | 5/2008 | Miga et al. | 382/131 |

(Continued)

FOREIGN PATENT DOCUMENTS

| | | |
|---|---|---|
| CN | 101065067 | 10/2007 |
| EP | 1 880 679 A1 * | 1/2008 |

(Continued)

OTHER PUBLICATIONS

Sunakawa et al, English Translation of JP 2007090003, 2007.*

*Primary Examiner* — Unsu Jung
*Assistant Examiner* — Serkan Akar
(74) *Attorney, Agent, or Firm* — Antonelli, Terry, Stout & Kraus, LLP.

(57) ABSTRACT

An ultrasonic diagnostic apparatus according to the present invention has an ultrasonic probe for transmitting/receiving an ultrasonic wave to/from an object while the object is pressed, a phasing and adding unit for generating RF signal frame data of a cross-sectional site of the object on the basis of a reflection echo signal measured by the ultrasonic probe, an ultrasonic image generating unit for generating an ultrasonic image of the cross-sectional site of the object on the basis of the RF signal frame data, a measurement target setting unit for setting a measurement target to the RF signal frame data or the ultrasonic image, a measurement target position tracing unit for tracing a positional variation of the set measurement target, a displacement image generating unit for generating a graph representing transition of a press state applied to the measurement target on the basis of the positional variation of the measurement target, and a display unit for displaying the generated graph.

10 Claims, 10 Drawing Sheets

(56) References Cited

U.S. PATENT DOCUMENTS

| | | | |
|---|---|---|---|
| 2008/0269606 A1* | 10/2008 | Matsumura | 600/438 |
| 2010/0268084 A1* | 10/2010 | Osaka et al. | 600/443 |
| 2011/0004100 A1* | 1/2011 | Iimura | 600/443 |

FOREIGN PATENT DOCUMENTS

| | | | |
|---|---|---|---|
| JP | 2000-060853 | | 2/2000 |
| JP | 2004-351062 | | 12/2004 |
| JP | 2005-270341 | A | 10/2005 |
| JP | 2007-090003 | | 4/2007 |
| JP | 2007-90003 | A | 4/2007 |
| JP | EP 1800603 | * | 6/2007 |
| JP | 2007-518508 | | 7/2007 |
| WO | WO 2005/070298 | | 8/2005 |
| WO | WO 2005/120358 | | 12/2005 |
| WO | WO 2006/013916 A1 | | 2/2006 |

* cited by examiner

ULTRASONIC ELASTOGRAPHY FOR CROSS SECTIONAL TISSUE MEASUREMENT METHOD AND APPARATUS

TECHNICAL FIELD

The present invention relates to an ultrasonic diagnostic apparatus, and particularly to an ultrasonic diagnostic apparatus, an ultrasonic image processing method and an ultrasonic image processing program with which an elasticity image representing hardness or softness of a tissue at a cross-sectional site of an object is picked up and displayed.

BACKGROUND ART

The ultrasonic diagnostic apparatus transmits an ultrasonic wave to the inside of an object by an ultrasonic probe, receives a reflection echo signal of an ultrasonic wave corresponding to the structure of a biometric tissue from the inside of the object, constructs an image such as an ultrasonic cross-sectional image or the like and displays the image for diagnosis.

It has been recently disclosed that an object is pressed by an ultrasonic probe according to a manual or mechanical method to measure an ultrasonic reception signal, a displacement of each part of a living body which is caused by the press is determined on the basis of frame data of two ultrasonic reception signals measured at different times, and an elasticity image representing elasticity of the biometric tissue is generated on the basis of the displacement data (for example, Patent Document 1).

From the viewpoint of easiness, an ultrasonic probe has been frequently used for an operation of pressing an object. That is, an ultrasonic probe is pressed against the body surface of an object to apply some degree of initial press, and an elasticity image is generated while minute pressurization and minute depressurization are repeated from this initial press state. However, according to this method, the pressurization state is greatly varied in accordance with an operator's hand operation, and thus there is a case where a proper elasticity image is not necessarily obtained.

Therefore, it is disclosed in a conventional ultrasonic diagnostic apparatus that a displacement of each site is measured on the basis of two tomographic image data measured at different times, a distribution of distortion factor of a tomographic image is determined on the basis of the displacement data, and properness of pressurization is determined on the basis of whether the distribution of distortion factor is within a proper range or not (for example, Patent Document 2).

Furthermore, it is also disclosed that a pressure sensor is provided to an object pressing face of an ultrasonic probe, and transition of measurement values of the pressure sensor is graphed and displayed together with an elasticity image (for example, Patent Document 3).

Patent Document 1: JP-A-2000-060853
Patent Document 2: JP-A-2004-351062
Patent Document 3: Publication of PCT application WO2005-120358

DISCLOSURE OF THE INVENTION

Problem to be Solved by the Invention

However, in the techniques described in the Patent Documents 2 and 3, it is not considered that a press state applied to a tissue of interest at a cross-sectional site of an object is presented to an operator with higher precision.

That is, the technique described in the Patent Document 2 estimates the press on the basis of the distortion distribution of a tissue in an area of a cross-sectional site. The distortion distribution also contains distortion data of surrounding tissues other than the tissue of interest, and thus there is a case where the press state applied to the tissue of interest cannot be determined with high precision.

Furthermore, when pressure sensor values of the pressing face of the ultrasonic probe are used as described in the Patent Document 3, the press intensity of the sensor surface is measured, and thus there is a case where a press state applied to a tissue of interest in an object cannot be directly reflected.

Therefore, it is a problem of the present invention to present a press state applied to a tissue of interest of a cross-sectional site of an object to an operator with high precision, thereby supporting a proper pressing operation.

Means of Solving the Problem

In order to solve the above problem, an ultrasonic diagnostic apparatus according to the present invention is characterized by comprising: an ultrasonic probe for transmitting/receiving an ultrasonic wave to/from an object while the object is pressed; a phasing and adding unit for generating RF signal frame data of a cross-sectional site of the object on the basis of a reflection echo signal measured by the ultrasonic probe; an ultrasonic image generating unit for generating an ultrasonic image of the cross-sectional site of the object on the basis of the RF signal frame data; a measurement target setting unit for setting a measurement target to the RF signal frame data or the ultrasonic image; a measurement target position tracing unit for tracing a positional variation of the set measurement target; a displacement image generating unit for generating a graph representing transition of a press state applied to the measurement target on the basis of the positional variation of the measurement target; and a display unit for displaying the generated graph.

Furthermore, an ultrasonic image processing method according to the present invention for generating an ultrasonic image from RF signal frame data of a cross-sectional site of the object which are based on a reflection echo signal measured by transmitting/receiving an ultrasonic wave to/from the object while the object is pressed by an ultrasonic probe, and generating an image for assisting the press of the object by the ultrasonic probe, is characterized by comprising: a step of setting a measurement target to the RF signal frame data or the ultrasonic image; a step of tracing a positional variation of the set measurement target; a step of generating a graph representing transition of a press state applied to the measurement target on the basis of a positional variation of the measurement target; and a step of displaying the generated graph.

An ultrasonic image processing program according to the present invention for making a computer execute a function of generating an ultrasonic image from RF signal frame data of the cross-sectional site of the object which are based on a reflection echo signal measured by transmitting/receiving an ultrasonic wave to/from the object while the object is pressed by an ultrasonic probe, and generating an image for assisting the press of the object by the ultrasonic probe, is characterized by making the computer execute: a step of setting a measurement target to the RF signal frame data or the ultrasonic image; a step of tracing a positional variation of the set measurement target; a step of generating a graph representing transition of a press state applied to the measurement target on the basis of the positional variation of the measurement target; and a step of displaying the generated graph.

That is, according to the present invention, a measurement target is set at a cross-sectional site of an object, and a graph representing transition of a press state such as a transition graph of a positional variation of the measurement target or the like is generated and displayed on the basis of a tracing result of the positional variation of the measurement target. Therefore, the transition of the press state applied to the measurement target of the cross-sectional site of the object is directly reflected to this graph with high precision. As a result, an operator can visually surely grasp the press state applied to the measurement target through an operation being executed by the operator, and thus it can be determined on the basis of the press state whether the pressing operation is proper or not.

Effect of the Invention

As described above, according to the ultrasonic diagnostic apparatus, the ultrasonic elasticity information processing method and the ultrasonic elasticity information processing program of the present invention, the press state applied to the tissue of interest of the cross-sectional site of the object can be presented to the operator with high precision, whereby the proper pressing operation can be supported.

DESCRIPTION OF REFERENCE NUMERALS 1 ultrasonic diagnostic apparatus, 10 object, 12 ultrasonic probe, 18 phasing and adding unit, 20 tomographic image constructing unit, 26 image display unit, 30 displacement measuring unit, 32 elasticity information calculator, 34 elasticity image constructing unit, 38 displacement calculator, 40 displacement image constructing unit, 42 operation unit, 44 tumor, 46 measurement point, 48, 53, 55 graph, 50 vibration threshold value line, 52 period line, 54 reference body, 60 threshold value Modes for Carrying Out the Invention Embodiments of an ultrasonic diagnostic apparatus to which the present invention is applied will be described. In the following description, parts having the same functions are represented by the same reference numerals and the duplicative description thereof is omitted.

Figure 1:
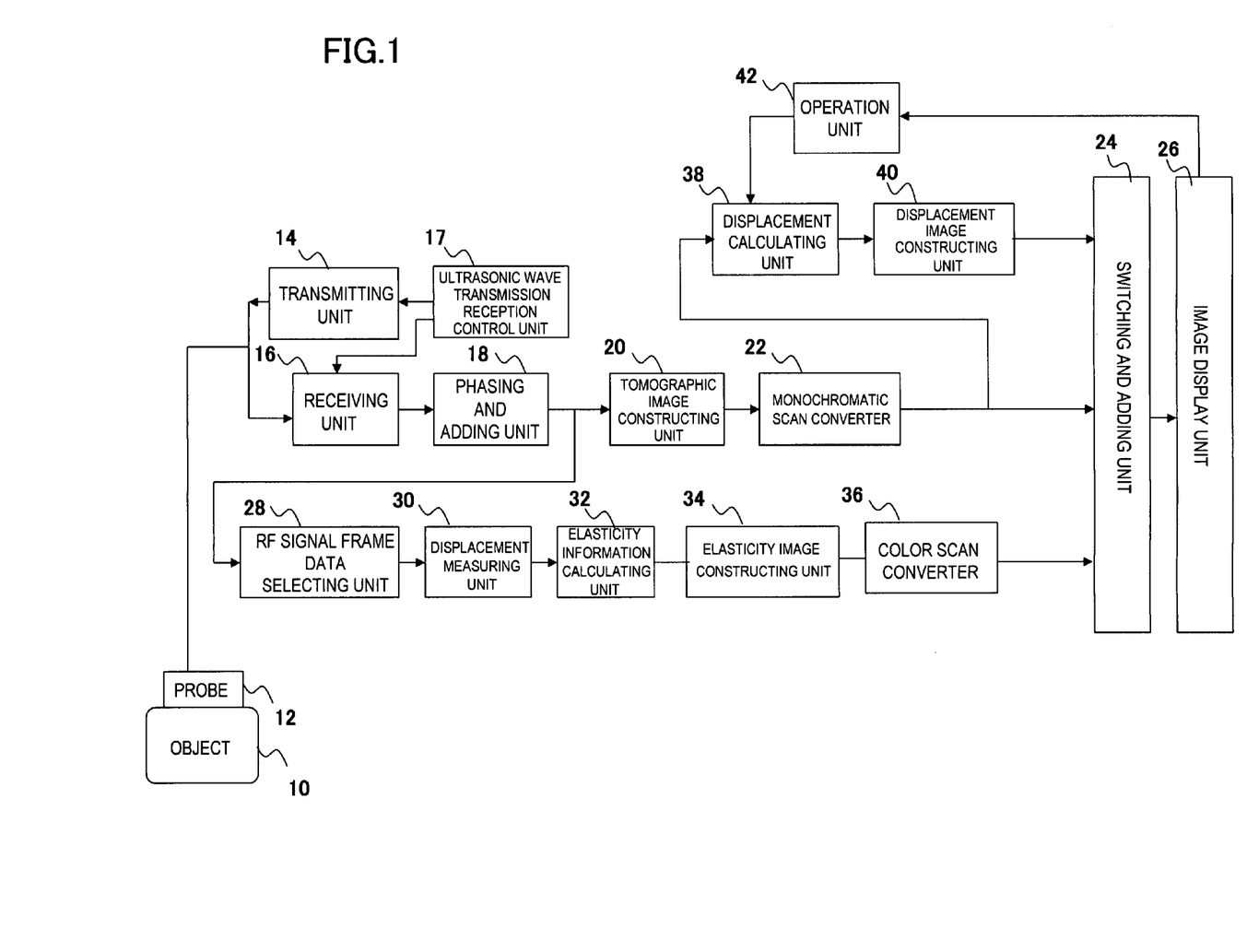
FIG. 1 is a block diagram showing the construction of an ultrasonic diagnostic apparatus according to an embodiment.

FIG. 1 is a block diagram showing the construction of an ultrasonic diagnostic apparatus of this embodiment. As shown in FIG. 1, the ultrasonic diagnostic apparatus 1 is equipped with an ultrasonic probe 12 which is used in contact with an object 10, a transmitting unit 14 for repetitively transmitting an ultrasonic wave to the object 10 through the ultrasonic probe 12 at a time interval, a receiving unit 16 for receiving time-series reflection eco signals occurring from the object 10, a transmission/reception controller 17 for controlling the transmitting unit 14 and the receiving unit 16 and a phasing and adding unit 18 for phasing and adding the reflection echoes received by the receiving unit 16.

Furthermore, a tomographic image constructing unit 20 for constructing a shading tomographic image, for example, a monochromatic tomographic image of the object on the basis of the RF signal frame data from the phasing and adding unit 18, and a monochromatic scan converter 22 for converting an output signal from the tomographic image constructing unit 20 so that the output signal is matched with display of an image display unit 26.

There are further provided an RF frame data selecting unit 28 for storing RF signal frame data output from the phasing and adding unit 18 and selecting at least two frame data, a displacement measuring unit 30 for measuring a displacement of a biometric tissue of the object 10, an elasticity information calculator 32 for determining distortion or elasticity modulus from the displacement information measured by the displacement measuring unit 30, an elasticity image constructing unit 34 for constructing a color elasticity image from the distortion or the elasticity modulus calculated by the elasticity information calculator 32, and a color scan converter 36 for converting an output signal of the elasticity image constructing unit 34 so that the output signal is matched with the display of the image display unit 26.

There are provided a switching and adding unit 24 for performing a switching operation of superimposing a monochromatic tomographic image and a color elasticity image or displaying them in parallel, and the image display unit 26 for displaying a combined composite image. The tomographic image constructing unit 20, the elasticity image constructing unit 34, etc. constitute ultrasonic image generating means for generating an ultrasonic image of a cross-sectional site of the object on the basis of the RF signal frame data.

Here, the respective constituent elements of the ultrasonic diagnostic apparatus 1 will be described in detail. The ultrasonic probe 12 is formed by arranging plural transducers, and it has a function of transmitting/receiving ultrasonic waves through the transducers to/from the object 10. The transmitting unit 14 has a function of driving the ultrasonic probe 12 to generate a wave-transmission pulse for generating an ultrasonic wave and also setting a convergence point of the ultrasonic wave to be transmitted to some depth. The receiving unit 16 amplifies a reflection echo signal received by the ultrasonic probe 12 with a predetermined gain to generate an RF signal, that is, a wave-reception signal. The phasing and adding unit 18 receives the RF signal amplified by the receiving unit 16 to perform phase control and forms an ultrasonic beam for one point or plural convergence points, thereby generating RF signal frame data.

The tomographic image constructing unit 20 receives the RF signal frame data from the phasing and adding unit 18 and executes signal processing such as gain correction, log compression, wave detection, edge enhancement, filter processing, etc. to obtain tomographic image data. Furthermore, the monochromatic scan converter 22 has an A/D converter for converting tomographic image data from the tomographic image constructing unit 20 to a digital signal, a frame memory for storing plural converted tomographic image data in time-series, and a control controller. The monochromatic scan converter 22 obtains in-object cross-sectional frame data stored in the frame memory as one image, and reads out the obtained cross-sectional frame data synchronously with TV.

The RF frame data selecting unit 28 stores plural RF signal frame data from the phasing and adding unit 18 and selects a pair of, that is, two RF signal frame data obtained at different times from the stored RF signal frame data group. For example, the RF signal frame data generated in time-series, that is, on the basis of an image frame rate from the phasing and adding unit 18 are successively stored into the RF frame data selecting unit 28, the stored RF signal frame data (N) is selected as first data and at the same time one RF signal frame data (X) is selected from RF signal frame data group (N-1, N-2, N-3, . . . , N-M) which were stored in the past. Here, N, M and X represent index numbers affixed to the RF signal frame data, and set to natural numbers.

The displacement measuring unit 30 executes one-dimensional or two-dimensional correlation processing on the selected one pair of data, that is, the RF signal frame data (N) and the RF signal frame data (X) to determine a one-dimensional or two-dimensional displacement distribution concerning the displacement and moving vector, that is, the direction and magnitude of the displacement of a biometric tissue which corresponds to each point of a tomographic image. Here, a block matching method is used to detect the moving vector. The block matching method is defined as the processing of dividing an image into blocks each of which comprises N×N pixels, for example, noting a block in an area of interest, searching from a previous frame a block which is most approximate to the block being noted, and refers to the searched block to determine a sample value through predictive coding, that is, differential calculation.

The elasticity information calculator 32 calculates the distortion and the elasticity modulus of a biometric tissue corresponding to each point on a tomographic image from a measured value output from the displacement measuring unit 30, for example, a displacement and a moving vector, and generates an elasticity image signal, that is, elasticity frame data on the basis of the distortion and the elasticity modulus.

At this time, the data of the distortion are calculated by spatially differentiating a moving amount, for example, a displacement of the biometric tissue. The data of the elasticity modulus is calculated by dividing the variation of pressure output from a pressure sensor (not shown) provided to the pressing face of the ultrasonic probe by the variation of distortion. For example, when the displacement measured by the displacement measuring unit 30 is represented by L(X) and the pressure measured by the pressure sensor is represented by P(X), the distortion $\Delta S(X)$ can be calculated by spatially differentiating L(X), and thus it can be determined by using the mathematical expression of $\Delta S(X)=\Delta L(X)/\Delta X$.

Furthermore, Young's modulus Ym(X) of the elasticity modulus data is calculated according to the mathematical expression of $Ym=(\Delta P(X))/\Delta S(X)$. The elasticity modulus of a biometric tissue corresponding to each point of a tomographic image is determined from the Young's modulus Ym, and thus two-dimensional elasticity image data can be continuously obtained. The Young's modulus represents the ratio of simple tension stress applied to an object to strain occurring in parallel to the tension.

The elasticity image constructing unit 34 is configured to contain a frame memory and an image processor, and it memorizes elasticity frame data output in time-series from the elasticity information calculator 32 into a frame memory and executes image processing on the thus-memorized frame data.

The color scan converter 36 has a function of adding hue information to the elasticity frame data from the elasticity image constructing unit 34. That is, it performs conversion to three primary colors of light, that is, red(R), green(G) and blue(B) on the basis of the elasticity frame data. For example, elasticity data having large distortion is converted to a red color code, and elasticity data having small distortion is converted to a blue color code at the same time.

The switching and adding unit 24 is configured to have a frame memory, an image processor and image selecting unit. The frame memory stores tomographic image data from the monochromatic scan converter 22, elasticity image data from the color scan converter 36, and image such as a graph from a displacement image constructing unit 40 described later. Furthermore, the image processor combines the tomographic image data and the elasticity image data held in the frame memory and the graph data representing transition of the press state applied to the tissue of interest with changing the composite rate thereof. Brightness information and hue information of each pixel of a composite image are obtained by adding respective information of a monochromatic tomographic image and a color elasticity image in the composite rate. Furthermore, the image selecting unit selects an image to be displayed on the image display unit 26 from the tomographic image data and the elasticity image data in the frame memory, and the composite image data of the image processor.

The feature portion of the ultrasonic diagnostic apparatus according to this embodiment will be described. As shown in FIG. 1, the ultrasonic diagnostic apparatus 1 according to this embodiment has a displacement calculator 38, the displacement image constructing unit 40 and an operation unit 42.

The displacement calculator 38 traces the positional variation of a set measurement point of the tomographic image data output from the monochromatic scan converter 22 to calculate the displacement. With respect to the setting of the measurement point, an operator may set the measurement point to a tissue of interest such as tumor or the like on a tomographic image displayed on the image display unit 26 through an input interface such as a keyboard, a mouse, a touch sensor or the like, or a tissue of interest such as tumor or the like may be automatically detected by the ultrasonic diagnostic apparatus to set the measurement point to the detected tissue of interest. That is, the means of setting a measurement point to a tissue of interest of RF signal frame data or an ultrasonic image is constructed by operator's input setting or automatic setting of the ultrasonic diagnostic apparatus.

For example when a measurement point is set on the image display unit 26, data representing the position of the measurement point is input to the displacement calculator 38 through the operation unit 42, and the displacement calculator 38 traces the positional variation of the measurement point of the tomographic image data on the basis of the input data. The displacement calculator 38 functions as means for tracing the positional variation of the set measurement point. The trace of the measurement point can be performed by using a method such as tracking or the like. With respect to automatic detection of a tissue of interest such as tumor or the like, means of binarizing an RF frame signal in accordance with the intensity of a reflection echo and regarding a low echo portion as tumor or the like may be adopted because the intensity of a reflection echo from tumor is small.

The displacement image constructing unit 40 generates a graph representing transition of a press state applied to a tissue of interest such as tumor or the like on the basis of the position variation of the measurement point output from the displacement calculator 38.

The ultrasonic diagnostic apparatus is provided with an input interface as described above, an output interface such as the image display unit 26, a memory for storing software programs and calculating means which can read and execute the software programs, whereby the functions of the means for setting the measurement point to the tissue of interest of the RF signal frame data or the ultrasonic image, the displacement calculator 38, the displacement image constructing unit 40, etc. can be constructed and executed by the software programs.

A style of setting a measurement point, a style of a generated graph, a style of generating an image for supporting user's proper pressing operation, etc. will be described by using specific embodiments.

First Embodiment

Figure 2:
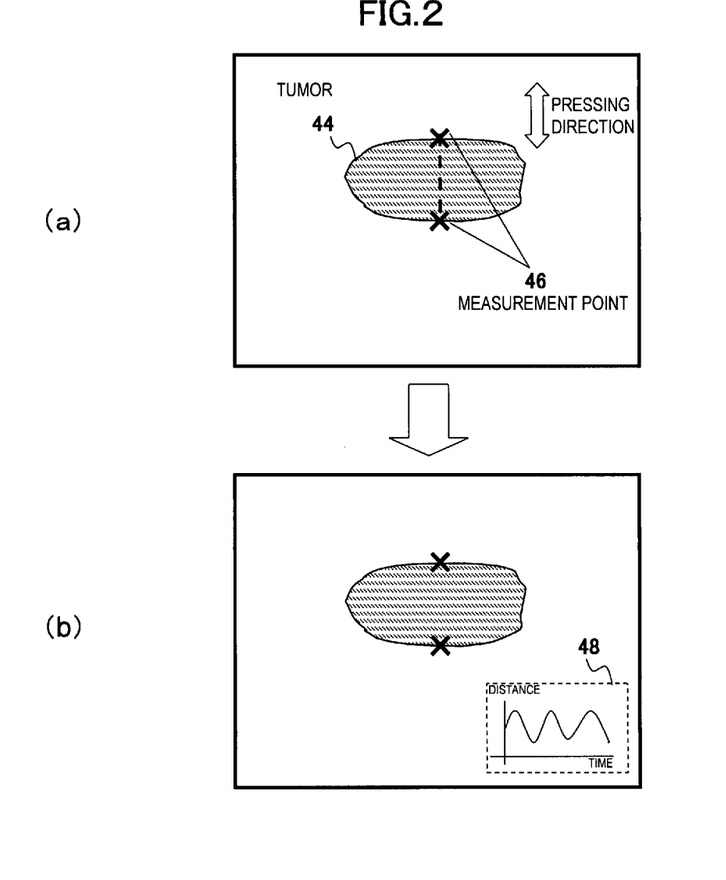
FIG. 2 is a diagram showing a first embodiment of a feature portion of the ultrasonic diagnostic apparatus.
Figure 3:
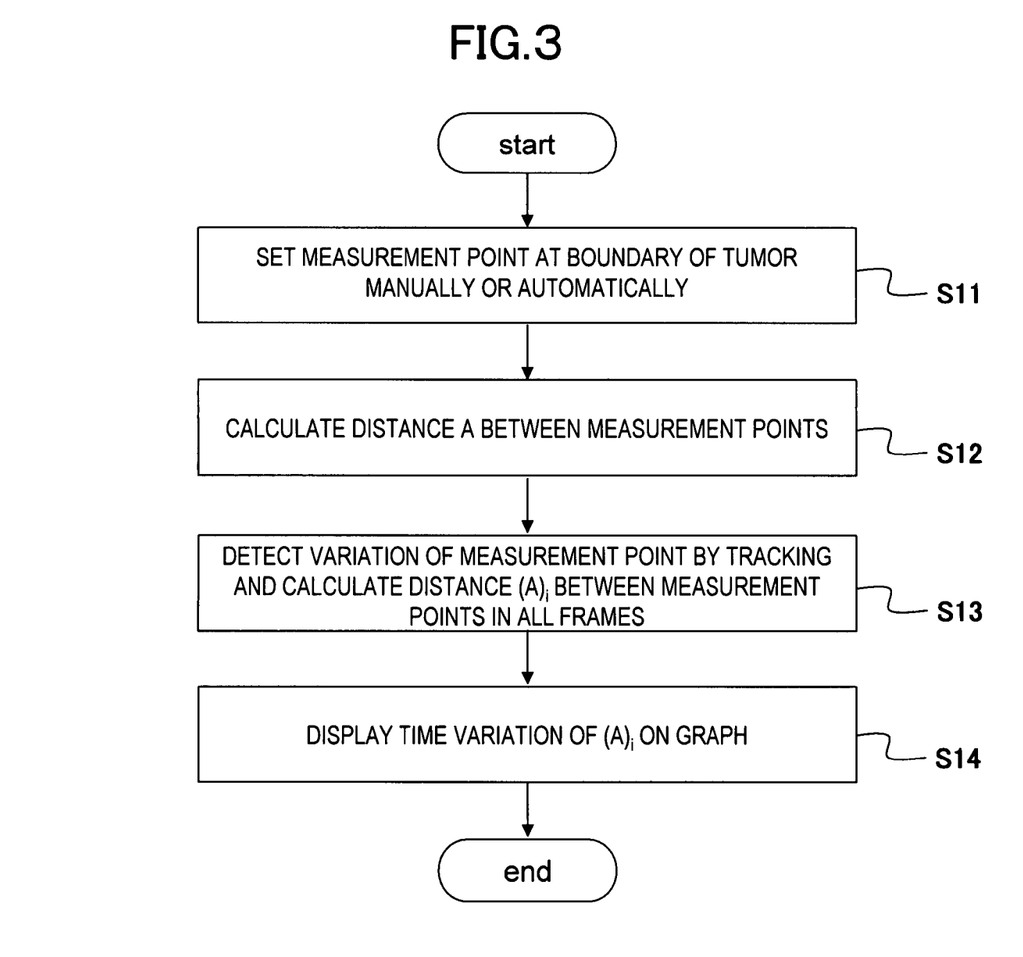
FIG. 3 is a flowchart showing the processing of the first embodiment.

FIG. 2 is a diagram showing a first embodiment of a feature portion of an ultrasonic diagnostic apparatus according to this embodiment, and schematically shows a setting example of the measurement point and a graph generated in this case. FIG. 3 is a flowchart showing the processing of the first embodiment.

As shown in FIG. 2(*a*), two measurement points 46 are set along a pressing direction at a boundary portion of tumor 44. The displacement calculator 38 traces the two measurement points every frame by tracking or the like, and it calculates the distance between the two measurement points with respect to all frame memory data, and successively the result to the displacement image constructing unit 40. The displacement image constructing unit 40 generates transition of the distance variation between the two measurement points in the form of a graph 48.

The graph 48 output from the displacement image constructing unit 40 is added and combined by the switching and adding unit 24, and it is displayed on the image display unit 26 together with an image obtained by superimposing a tomographic image and an elasticity image as shown in FIG. 2(*b*).

Next, the operation of the first embodiment will be described with reference to the flowchart of FIG. 3. First, data obtained from the monochromatic scan converter 22 are subjected to binarization processing, whereby the two measurement points 46 are set along the pressing direction at the boundary of tumor corresponding to a tissue of interest automatically or manually through the operation unit 42 (S11). Subsequently, the distance A between the measurement points set in the displacement calculator 38 is detected (S12). Furthermore, the positions of the measurement points which vary due to press are detected by tracking, and the distance (A)i between the measurement points in all the frame memories is detected (S13). Subsequently, the graph 48 representing the displacement of the tissue is generated from (A)i in the displacement image constructing unit 40, and displayed on the image display unit 26 through the switching and adding unit 24 (S14).

According to this embodiment, the two measurement points are set along the direction along which the tissue of interest of the cross-sectional site of the object is pressed, the graph of the transition of the distance variation between the measurement points, in other words, the graph representing the transition of the press state is generated and displayed. Therefore, the transition of the press state applied to the tissue of interest of the cross-sectional site of the object is directly reflected to the graph with high precision. As a result, the operator can visually and surely grasp the press state applied to the tissue of interest by the operation which is being executed by himself/herself. Therefore, it can be determined on the basis of this grasping whether the pressing operation is proper or not.

It is possible to set only one measurement point and graph the traced position variation of the measurement point. However, by graphing the transition of the distance between two measurement points as in the case of this embodiment, the transition of the press state applied to the tissue of interest can be presented to the operator with higher precision.

Second Embodiment

Figure 4:
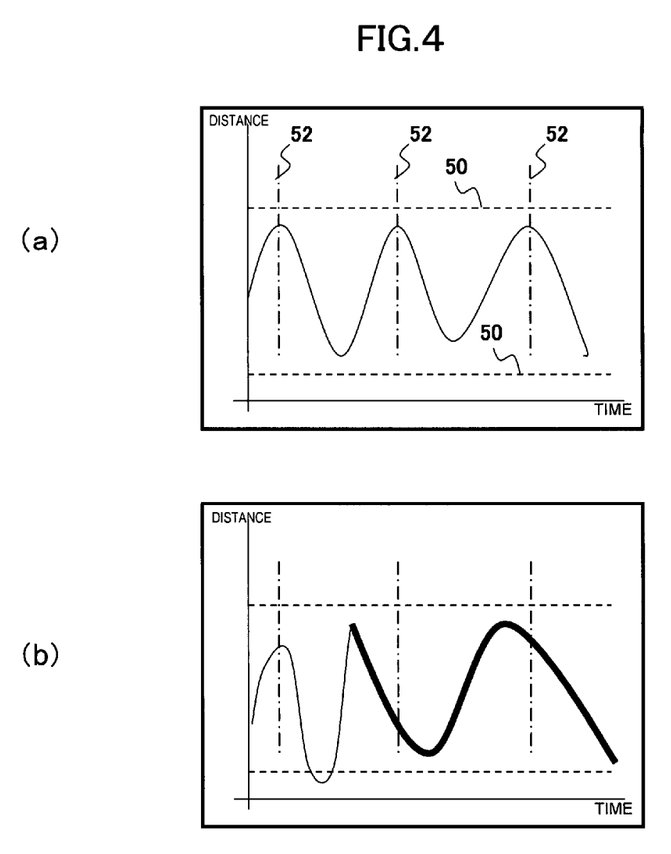
FIG. 4 is a diagram showing a second embodiment of the feature portion of the ultrasonic diagnostic apparatus.
Figure 5:
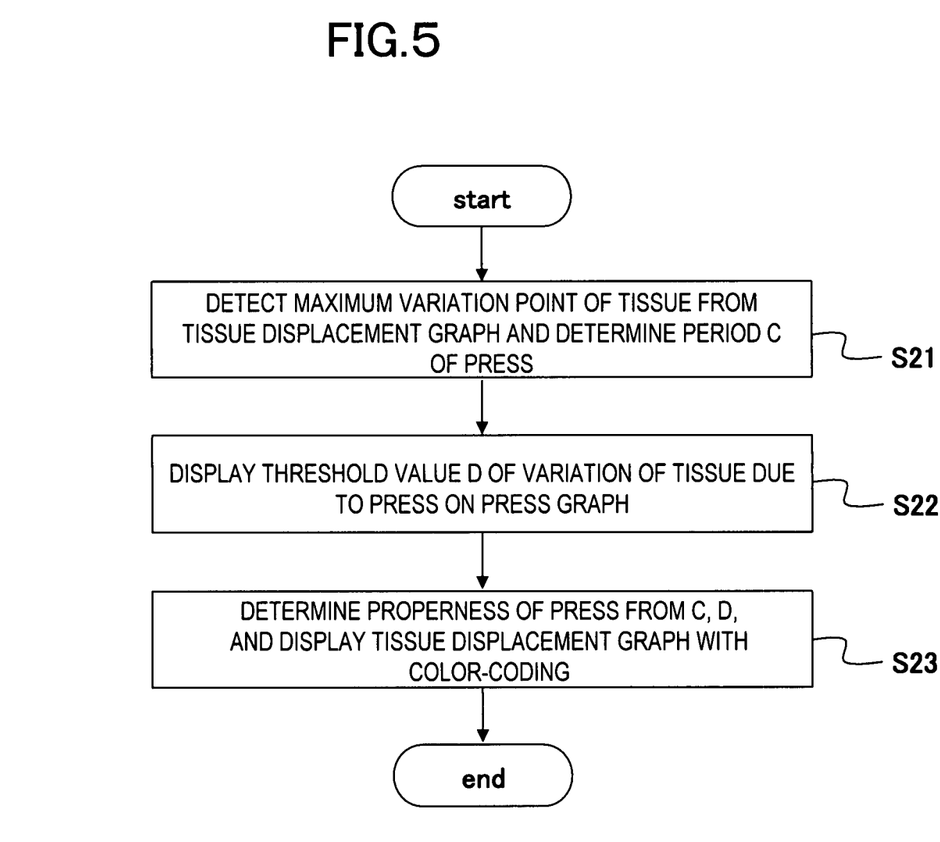
FIG. 5 is a flowchart showing the processing of the second embodiment.

FIG. 4 is a diagram showing a second embodiment of the feature portion of the ultrasonic diagnostic apparatus according to this embodiment, and shows an image generated to support the operator's proper pressing operation. FIG. 5 is a flowchart showing the processing of the second embodiment.

In this embodiment, the center position of the graph is determined on the basis of plural local maximum points and local minimum points appearing on the graph 48, an amplitude threshold value line is superimposed and displayed at a predetermined amplitude position from the center position of the graph 48, and also a preset period line is superimposed and displayed on the graph 48.

Furthermore, the display style of a place at which at least one of the period line and the amplitude threshold value line on the graph 48 is deviated is changed to promote a proper pressing operation to the operator.

Specifically, as shown in FIG. 4(*a*), preset period lines 52 are superimposed and displayed on the graph 48 generated as in the case of the first embodiment for example, whereby a proper period can be visually presented to the operator.

Furthermore, with respect to the graph 48, each local maximum point of the distance between measurement points is detected to detect a period C between the respective local maximum points, and the whole period (C)ave can be calculated according to the following expression.

$$(C)\text{ave} = (\Sigma(\text{period } C \text{ between respective local maximum points}))/(\text{number of local maximum points}-1)$$

As described above, (C)ave based on the operator's operation is determined by the calculation, whereby the degree of the difference from a preset recommended period can be detected by a numerical value, and this numerical value can be presented to the operator.

With respect to the graph 48, each local maximum point and each local minimum point for the distance between measurement points are detected to calculate each intermediate position of the distance between the measurement points, and the intermediate value (D)ave of the distance between measurement points for the overall press is calculated according to the following expression, whereby the threshold value of the amplitude can be displayed.

$$(D)\text{ave} = (\Sigma(\text{each center point position}))/(\text{number of local maximum points})$$

That is, when (D)ave is determined as described above, an amplitude threshold value line 50 having a predetermined width can be superimposed and displayed in the up-and-down direction of the amplitude of the graph 48, whereby a proper amplitude can be visually presented to the operator. The recommended period and amplitude may be suitably changed in accordance with a target tissue and saved, and a target site may be selected or arbitrarily input by the operator.

As shown in FIG. 4(b), the properness of press can be determined and presented to the operator by using the period lines 52 and the amplitude threshold value line 50 superimposed on the graph 48. That is, press causing deviation from the amplitude threshold value line 50 or press causing deviation from the period lines 52 is determined as improper press, and the color of the corresponding place on the graph 48 is changed and displayed. Accordingly, the operator can easily determine the properness of the press visually.

Next, the operation of the second embodiment will be described with reference to FIG. 5. First, the preset recommended period lines 52 are superimposed on the graph 48 (S21). Subsequently, the intermediate value (D)ave of the distance between the measurement points of the whole press is calculated, and the amplitude threshold value line 50 having the predetermined width is superimposed in the up-and-down direction from the intermediate value (S22). The press causing the deviation from the amplitude threshold value line 50 or the press causing the deviation from the period lines 52 is determined as improper press, and the color of the corresponding place of the tissue displacement graph is changed (S23).

Third Embodiment

Figure 6:
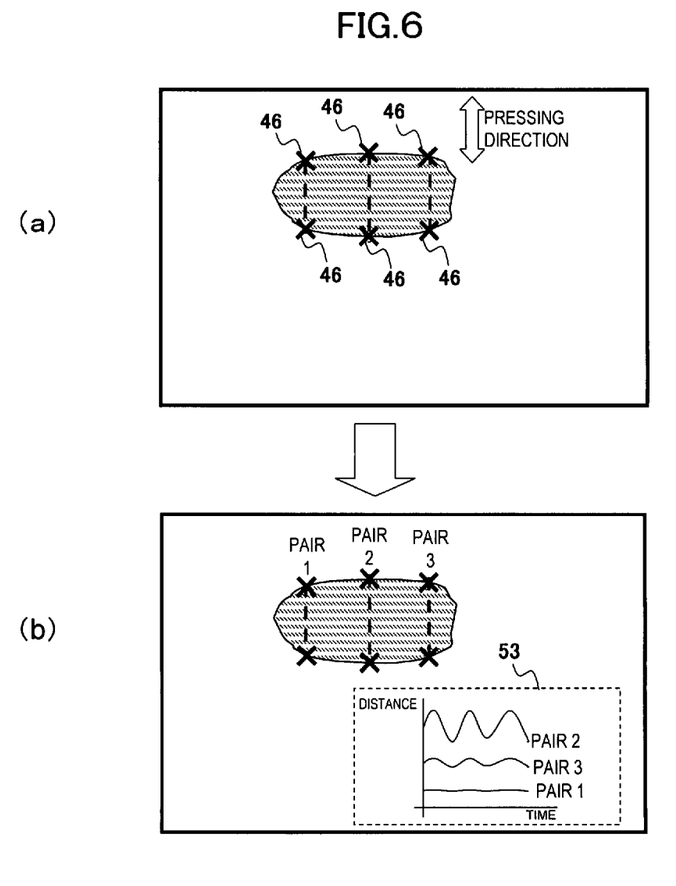
FIG. 6 is a diagram showing a third embodiment of the feature portion of the ultrasonic diagnostic apparatus.
Figure 7:
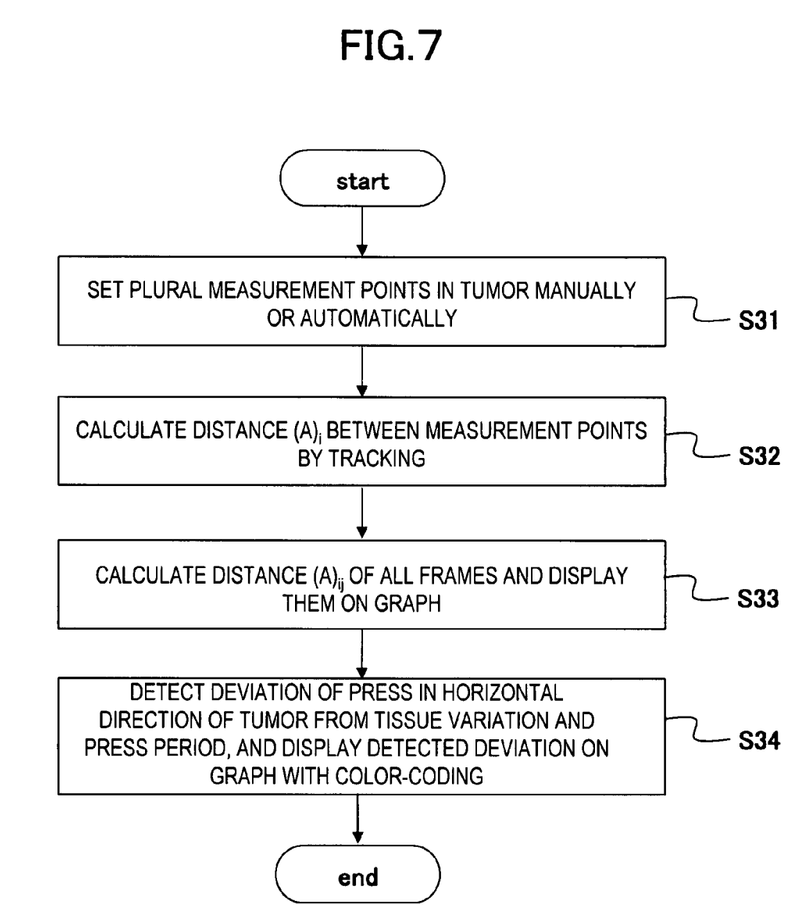
FIG. 7 is a flowchart showing the processing of the third embodiment.

FIG. 6 is a diagram showing a third embodiment of the feature portion of the ultrasonic diagnostic apparatus according to this embodiment, and schematically shows a setting example of the measurement point and a graph generated in this case. FIG. 7 is a flowchart showing the processing of the third embodiment.

As shown in FIG. 6(a), plural pairs of two measurement points along the pressing direction at the boundary portion of the tumor 44 are set at different positions in a direction perpendicular to the pressing direction. The displacement calculator 38 traces each measurement point every frame by tracking or the like, calculates the distance between the paired measurement points for all the frame memory data every pair of two measurement points, and successively outputs the calculation result to the displacement image constructing unit 40. The displacement image constructing unit 40 generates the transition of the distance variation between the measurement points in the form of a graph 53 every pair of two measurement points.

The graph 53 output from the displacement image constructing unit 40 is added and combined by the switching and adding unit 24, and displayed on the image display unit 26 together with an image in which the tomographic image and the elasticity image are superimposed as shown in FIG. 6(b). That is, when the pairs of the measurement points 46 are represented by pair 1, pair 2 and pair 3 in this order from the left side of the figure, the transitions of the distance variation between the measurement points for the pair 1 to the pair 3 are displayed to be arranged in the vertical direction.

Next, the operation of the first embodiment will be described with reference to the flowchart of FIG. 7. First, the data obtained from the monochromatic scan converter 22 are subjected to binarization processing to set plural pairs (for example, pair 1 to pair 3) of two measurement points 46 along the pressing direction at the boundary of tumor as a tissue of interest automatically or manually through the operation unit 42 (S31). Subsequently, for each of the pair 1 to the pair 3, the distance A between the measurement points set in the displacement calculator 38 is detected (S32). Furthermore, the position of the measurement points which varies due to press is detected by tracking, and the distance (A)i between the measurement points in all the frame memories is detected for each of the pair 1 to the pair 3 (S33). Subsequently, for each of the pair 1 to the pair 3, the graph 53 representing the displacement of the tissue is generated from (A)i in the displacement image constructing unit 40, and displayed on the image display unit 26 through the switching and adding unit 24 (S34).

According to this embodiment, by referring each of these graphs, the operator can determine whether the whole tumor as the tissue of interest is pressed with uniform force with respect to the horizontal direction perpendicular to the pressing direction, in other words, whether the tumor is not eccentrically pressed or not.

That is, when the whole tumor is uniformly pressed, the distances of all the measurement point pairs vary substantially at the same period and amplitude in the generated graph, and thus it is determined that that there is no deviation in press. On the other hand, for example when there is some dispersion in amplitude among the pair 1 to the pair 3 as shown in FIG. 6(b), it can be determined that the press is eccentrically applied to the pair 3 having large amplitude, and thus it is necessary to readjust the pressing direction.

The graph display corresponding to each pair of measurement points may be displayed with a name so that the corresponding relationship between the pair of the measurement points and the graph is clear as shown in FIG. 6(b), or the corresponding relationship may be displayed by another method such as color-coding or the like.

Fourth Embodiment

Figure 8:
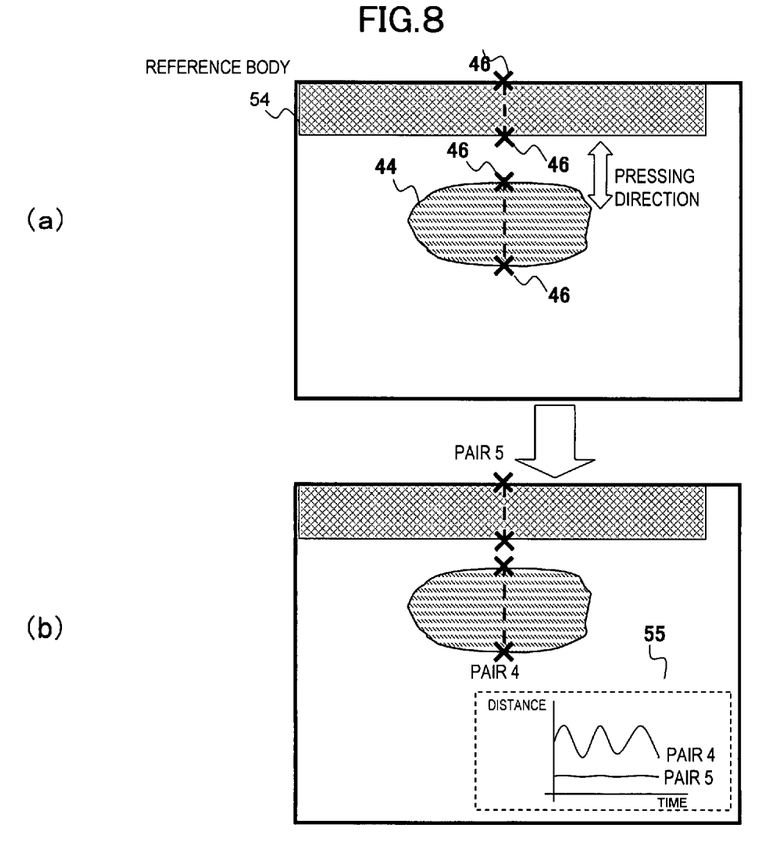
FIG. 8 is a diagram showing a fourth embodiment of the feature portion of the ultrasonic diagnostic apparatus.
Figure 9:
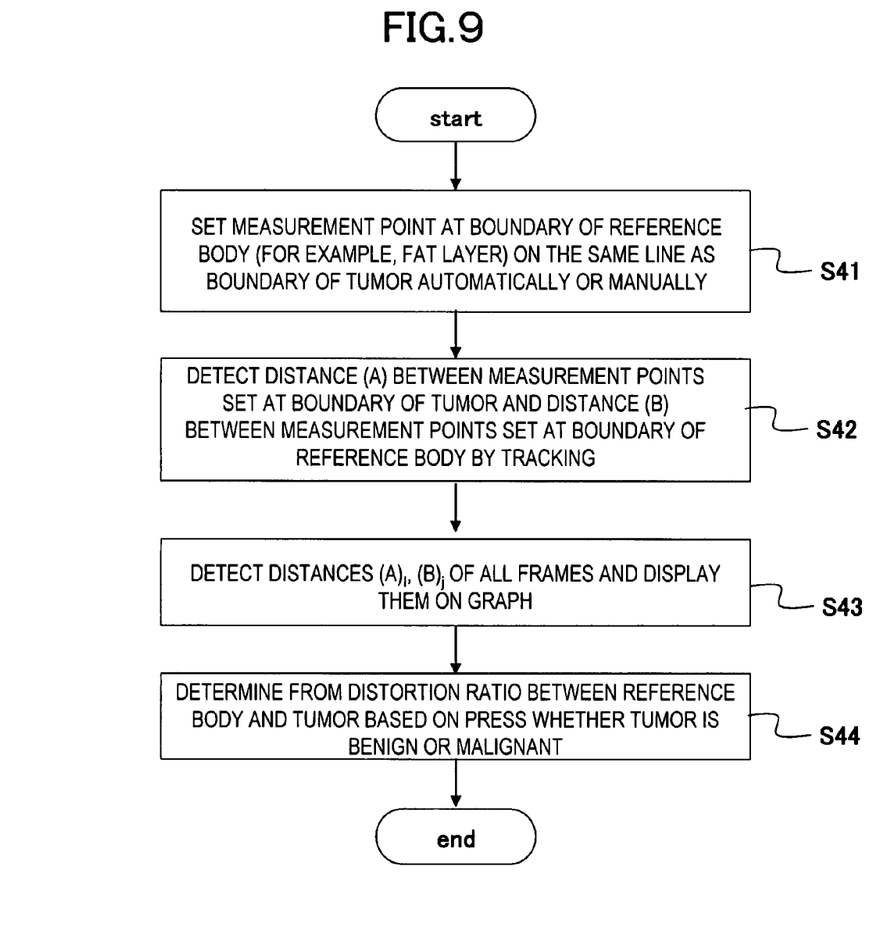
FIG. 9 is a flowchart showing the processing of the fourth embodiment.

FIG. 8 is a diagram showing a fourth embodiment of the feature portion of the ultrasonic diagnostic apparatus according to this embodiment, and schematically shows a setting example of the measurement points and a graph generated in this case. FIG. 9 is a flowchart showing the processing of the fourth embodiment.

As shown in FIG. 8(a), this embodiment is identical to the first embodiment in that two measurement points 46 are set along the pressing direction at the boundary portion of the tumor 44. In this embodiment, two measurement points 46 are set along the pressing direction of a reference body 54 as a displacement reference for the press.

As the reference body 54 may be targeted a fat layer of an object or a pressing plate provided to the pressing face of the probe. That is, the fat layer is relatively small in the individual difference between the objects, and the average displacement amount to the press has been already known. With respect to the pressing plate, the displacement amount to press has been already known. Therefore, they may be applied as the reference body 54 as a displacement reference to the press.

The displacement calculator 38 traces each measurement point every frame by tracking or the like, calculates the distance between measurement points for all the frame memory data every pair of two measurement points of the tumor 44 and every pair of two measurement points of the reference body 54, and successively outputs the calculation result to the displacement image constructing unit 40. The displacement image constructing unit 40 generates the transition of the distance variation between the measurement points in the form of a graph 55 every pair of two measurement points.

The graph 55 output from the displacement image constructing unit 40 is added and combined by the switching and adding unit 24, and displayed on the image display unit 26 together with an image in which a tomographic image and an elasticity image are superimposed as shown in FIG. 8(b). That is, when the pair of measurement points of the tumor 44 is represented by a pair 4 and a pair of measurement points of the reference body 54 is represented by a pair 5, the transitions of the distance variation between the measurement points for the pairs 4 and 5 are displayed so as to be arranged in the vertical direction.

Next, the operation of the fourth embodiment will be described with reference to the flowchart of FIG. 9. First, the data obtained from the monochromatic scan converter 22 are subjected to binarization processing, whereby two measurement points 46 are set in the pressing direction at the boundary of the tumor as the tissue of interest automatically or manually through the operation unit 42, and further the measurement points 46 are set to the reference body 54 in the same pressing direction (S41).

Subsequently, the distance A between the measurement points 46 set in the tumor is detected by the displacement calculator 38, and also the distance B between the measurement points 46 set in the reference body is detected (S42). Furthermore, the position of the measurement point varying due to the press is also detected by tracking, and the distances (A)i, (B)i between the measurement points in all the frame memories are detected for the tumor and the reference body (S43). Subsequently, the graph 55 representing the displacement of the tissue is generated from (A)i, (B)i in the displacement image constructing unit 40 for each of the tumor and the reference body, and displayed on the image display unit 26 through the switching and adding unit 24 (S44).

Furthermore, the hardness of the tumor can be detected with reference to the reference body from the ratio of distortion between the reference body and the tumor which is caused by the press. That is, the ratio (A)i/(B)i of the distance of the measurement points between the tumor and the reference body in each frame memory may be calculated as a distortion ratio, and displayed as the calculation result on the image display unit 26. Accordingly, the displacement amount caused by the press can be compared with that of the reference body which has been already known, and thus the determination as to whether the tumor is benign or malignant can be simply performed.

When the reference body 54 is provided as in the case of this embodiment, this is particularly effective to a case where it is determined that initial press is proper or not. That is, it is general in the pressing operation of the ultrasonic probe that the ultrasonic probe is pressed against the body surface of the object to apply some degree of initial press, minute pressurization and minute depressurization are repeated from this initial press state. In order to generate a proper elasticity image, the degree of the initial press is an important factor.

Figure 10:
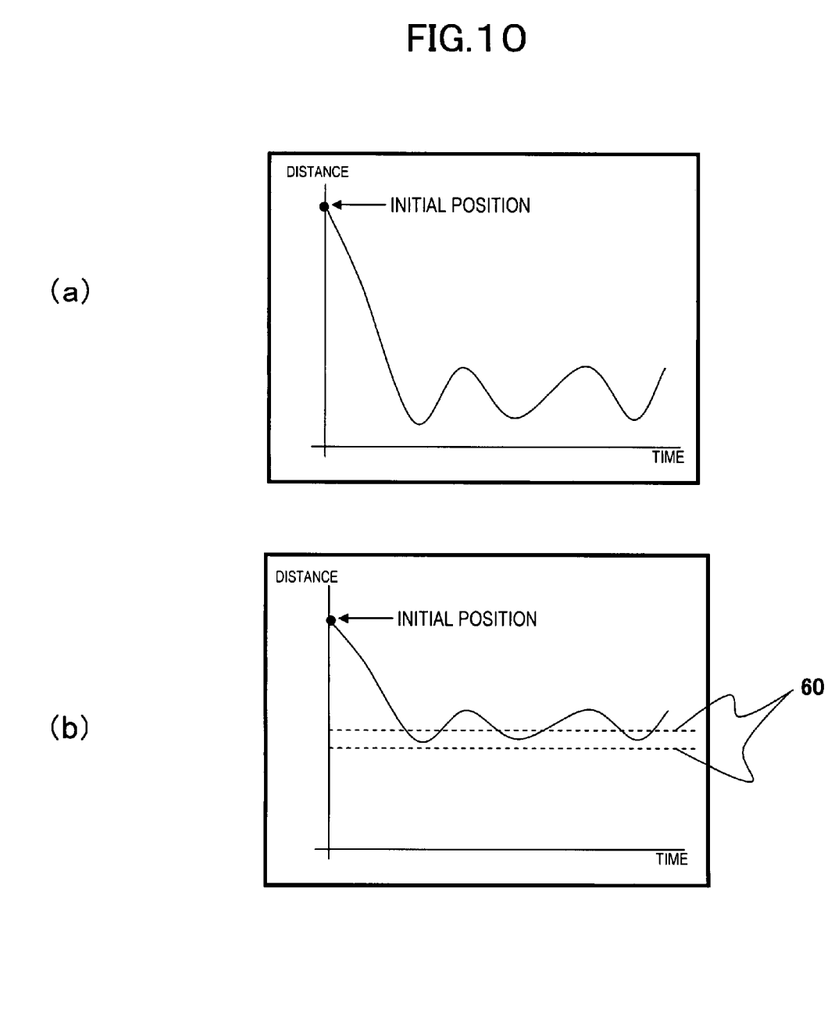
FIG. 10 is a schematic diagram to explain whether initial press is proper or not.

FIG. 10 is a schematic diagram for explaining whether the initial press is proper or not. FIG. 10(a) shows a case where the initial press is excessively strong. When elastography measurement is executed under the state that strong initial press is applied, minute press is applied to a soft tissue under the state that the tissue is crashed, and thus the hardness of the tissue cannot be accurately displayed.

On the other hand, as shown in FIG. 10(b), when two measurement points are set to the reference body before press is started, a graph representing the transition of the distance between the measurement points due to press is displayed and a threshold value 60 in a proper initial press range is set and displayed, the operator can perform proper initial press by referring to the threshold value 60. Only one measurement point may be set to display the transition of the displacement of the measurement point in the form of a graph. In this case, the proper threshold value corresponding to the graph is separately set. Furthermore, only the graph based on the measurement points set in the reference body is displayed in FIG. 10.

However, as shown in FIG. 8, it may be displayed in combination with the graph based on the measurement points set in the tumor.

As described above, the measurement points are set to the reference body for which some degree of displacement to press is set in advance, and the graph based on the displacement of the measurement points is displayed, whereby the operation can be performed with this graph as a criterion for determination so that the initial press amount is proper.

The ultrasonic diagnostic apparatus of this embodiment has been described above, however, the present invention is not limited to this embodiment. For example, when the measurement point is set, the measurement point is traced by using data output from the monochromatic scan converter 22, and the transition of the press state applied to the tissue of interest is graphed. However, the trace and the graphing can be performed by using RF signal frame data. Furthermore, the displacement measuring unit 30 may be commonly used to generate an elasticity image and detect the positional variation of a measurement point, and the transition of the press state applied to the tissue of interest may be graphed on the basis of the output from the displacement measuring unit 30.

Furthermore, in place of the measurement point, a measurement line, surface or the like may be set as a measurement target. Furthermore, in the above example, the ultrasonic image and the graph are displayed in juxtaposition with each other on the display unit. However, the present invention is not limited to this style, and at least graph may be displayed. For example, only a graph may be displayed to execute statistical analysis of press, and the difference between a skilled person and an unskilled person may be clarified, so that the graph is used for education for unskilled persons.

The invention claimed is:

1. An ultrasonic diagnostic apparatus comprising:
   an ultrasonic probe configured to transmit/receive an ultrasonic wave to/from an object, while the object is pressed in a pressing direction; and
   a controller including:
      a phasing and adding unit configured to generate RF signal frame data of a cross-sectional site of the object, on a basis of a reflection echo signal measured by the ultrasonic probe;
      an ultrasonic image generating unit configured to generate an ultrasonic image of the cross-sectional site of the object, on a basis of the RF signal frame data;
      a measurement target setting unit configured to set a measurement target to the RF signal frame data or the ultrasonic image, where the measurement target is two measurement points in line along a same pressing direction, at respective boundary portions of a tissue of interest within the object;
      a measurement target position tracing unit configured to trace a positional variation of the set measurement target;
      a displacement image generating unit configured to generate a graph representing transition of a press state applied to the measurement target on a basis of the positional variation of the measurement target;
      an elasticity image constructing unit for generating an elasticity image representing hardness or softness of a tissue of the cross-sectional site of the object on a basis of a pair of RF signal frame data obtained at different times; and
      a display unit configured to display the ultrasonic image, the elasticity image and the generated graph on a display while being associated with each other.

2. The ultrasonic diagnostic apparatus according to claim 1, wherein the ultrasonic image generating unit includes a tomographic image generating unit a tomographic image of a cross-sectional site of the object.

3. The ultrasonic diagnostic apparatus according to claim 1, wherein the measurement target setting unit sets the two measurement points along the pressing direction of the RF signal frame data of the tissue of interest of the ultrasonic image, and the displacement image generating unit generates a transition of distance variation between the two set measurement points as the graph.

4. The ultrasonic diagnostic apparatus according to claim 1, wherein the measurement target setting unit sets plural pairs of two measurement points along the pressing direction to a tissue of interest of the RF signal frame data or the ultrasonic image, at different positions in a direction perpendicular to the pressing direction, and the displacement image generating unit generates a graph of transition of distance variation regarding every pair of two measurement points.

5. The ultrasonic diagnostic apparatus according to claim 1, wherein the measurement target setting unit sets a reference measurement point to a reference body as a reference of displacement caused by the press in the RF signal frame data or the ultrasonic image, and the displacement image generating means generates a graph of transition of variation of the reference measurement point set in the reference body.

6. The ultrasonic diagnostic apparatus according to claim 1, wherein the displacement image generating unit determines a center position of the graph representing the transition of the press state applied to the measurement target on a basis of plural local maximum points and local minimum points of the graph, superimposing and displaying an amplitude threshold value line at a predetermined amplitude position from the center position of the graph on the display unit, and also superimposing and displaying a preset period line on the display unit.

7. The ultrasonic diagnostic apparatus according to claim 6, wherein the displacement image generating unit changes a display style for displaying onto the display unit with respect to a place at which the transition of the press state deviates from at least one of the period line and the amplitude threshold value line of the graph.

8. An ultrasonic image processing method for generating an ultrasonic image from RF signal frame data of a cross-sectional site of an object, which RF signal frame data are based on a reflection echo signal measured by transmitting/receiving an ultrasonic wave to/from the object while the object is pressed in a pressing direction by an ultrasonic probe, and for generating an image for assisting the press of the object by the ultrasonic probe, the ultrasonic image processing method comprising:
   setting a measurement target to the RF signal frame data or the ultrasonic image, where the measurement target is two measurement points in line along a same pressing direction, at boundary portions of a tissue of interest within the object;
   tracing a positional variation of the set measurement target;
   generating an elasticity image representing hardness or softness of a tissue of the cross-sectional site of the object on a basis of a pair of RF signal frame data obtained at different times;
   generating a graph representing transition of a press state applied to the measurement target on a basis of a positional variation of the measurement target; and
   displaying the ultrasonic image, the elasticity image and the generated graph on a display while being associated with each other.

9. A non-transitory computer readable medium embodying an ultrasonic image processing program for making a computer execute a function of generating an ultrasonic image from RF signal frame data of a cross-sectional site of an object, which RF signal frame data are based on a reflection echo signal measured by transmitting/receiving an ultrasonic wave to/from the object while the object is pressed in a pressing direction by an ultrasonic probe, and for generating an image for assisting the press of the object by the ultrasonic probe, the program making the computer execute:
   setting a measurement target to the RF signal frame data or the ultrasonic image, where the measurement target is two measurement points in line along a same pressing direction, at boundary portions of a tissue of interest within the object;
   tracing a positional variation of the set measurement target;
   generating an elasticity image representing hardness or softness of a tissue of the cross-sectional site of the object on a basis of a pair of RF signal frame data obtained at different times;
   generating a graph representing transition of a press state applied to the measurement target on a basis of a positional variation of the measurement target; and
   displaying the ultrasonic image, the elasticity image and the generated graph on a display while being associated with each other.

10. An ultrasonic image processing method for generating an ultrasonic image from RF signal frame data of a cross-sectional site of an object, which RF signal frame data are based on a reflection echo signal measured by transmitting/receiving an ultrasonic wave to/from the object while the object is pressed in a pressing direction by an ultrasonic probe, and for generating an image for assisting the press of the object by the ultrasonic probe, the ultrasonic image processing method comprising:
   setting a reference measurement target to the RF signal frame data or the ultrasonic image, where the reference measurement target is two measurement points in line along a same pressing direction, within a reference object;
   setting a measurement target to the RF signal frame data or the ultrasonic image, where the measurement target is two measurement points in line along a same pressing direction, at boundary portions of a tissue of interest within the object;
   tracing a positional variation of the set reference measurement target and the set measurement target;
   generating an elasticity image representing hardness or softness of the reference object and of a tissue of the cross-sectional site of the object, on a basis of a pair of RF signal frame data obtained at different times;
   generating graphs representing transition of a press state applied to the reference measurement target and the measurement target, respectively, on a basis of a positional variation of the measurement target; and
   displaying the ultrasonic image, the elasticity image and the generated graphs on a display, while being associated with each other.

* * * * *